United States Patent [19]

Marquardt et al.

[11] Patent Number: 5,120,654
[45] Date of Patent: Jun. 9, 1992

[54] CLONING AND USE OF THE TRANSAMINASE GENE ILVE

[75] Inventors: Rüdiger Marquardt, Frankfurt am Main; Johann Then; Hans-Matthias Deger, both of Hofheim am Taunus; Gerhard Wöhner, Flörsheim am Main, all of Fed. Rep. of Germany; Martyn K. Robinson, Maidenhead; Evelyn L. K. Doherty, Bourne End, both of Great Britain

[73] Assignee: Hoechst Aktiengesellschaft, Frankfurt am Main, Fed. Rep. of Germany

[21] Appl. No.: 566,320

[22] Filed: Aug. 13, 1990

Related U.S. Application Data

[63] Continuation of Ser. No. 112,932, Oct. 27, 1987, abandoned.

[30] Foreign Application Priority Data

Oct. 29, 1986 [DE] Fed. Rep. of Germany ....... 3636722

[51] Int. Cl.$^5$ .................... C12N 1/21; C12N 15/52; C12N 15/70

[52] U.S. Cl. .................. 435/252.33; 435/69.1; 435/71.2; 435/91; 435/108; 435/172.1; 435/172.3; 435/320.1; 435/849; 536/27; 935/6; 935/9; 935/14; 935/22; 935/24; 935/29; 935/33; 935/38; 935/59; 935/60; 935/61; 935/66

[58] Field of Search ............ 435/69.1, 71.2, 91, 435/172.1, 172.3, 252.33, 108, 320.1, 849; 536/27; 935/6, 9, 14, 22, 24, 29, 33, 38, 59, 60, 61, 66, 73

[56] References Cited

FOREIGN PATENT DOCUMENTS 0116860 8/1984 European Pat. Off. .

OTHER PUBLICATIONS

Shimatake et al., Nature 292, pp. 128–131, 1981.
Kuramitsu et al., J. Biochem. 97, pp. 993–999 (1985).

Primary Examiner—Richard C. Peet
Attorney, Agent, or Firm—Finnegan, Henderson, Farabow, Garrett and Dunner

[57] ABSTRACT

The ilvE gene from the strain *E. coli* ATCC 11303 is suitable for achieving overproduction of the coded aliphatic transaminase and thus for preparing the branched-chain amino acids leucine, isoleucine and valine from the corresponding keto precursors.

2 Claims, No Drawings

CLONING AND USE OF THE TRANSAMINASE GENE ILVE

This application is a continuation of application Ser. No. 07/112,932, filed Oct. 27, 1987 now abandoned.

The last step in the de novo synthesis of aliphatic amino acids comprises the amination of the corresponding keto precursors by means of a transaminase. Although various transaminases are able to carry out transamination reactions which result in aliphatic amino acids, this function is performed in the cell mainnly by what is called aliphatic transaminase. The abbreviation used in genetics for the gene for aliphatic transaminase is ilvE (Umbarger, Ann. Rev. Biochemistry 47 (1978), 533–606). In the case of E. coli K12, the location of the gene on the "bacterial chromosome" is known accurately, and the gene product has been given the E.C. number 2.6.1.42 (Bachmann et al., Microbiological Reviews 44 (1980), 1–56).

European Patent Application (EP-A) 0 116 860 describes the isolation of the ilvE gene from E. coli K12 and the cloning of this aminotransferase gene onto a multicopy plasmid. However, no specific data are given on the activity of the cloned ilvE gene product. There is a mention in EP-A 0 152 275 that an increase in the enzyme activity can be achieved by cloning of the ilvE gene. However, there are no data on an increase in the yield of aliphatic amino acids.

It has now been found, surprisingly, that isolation of the ilvE gene present in E. coli ATCC 11303, and its cloning onto a multicopy plasmid, results, after transformation of the starting strain with this plasmid, in an increase of at least 3- to 5-fold in the yield of the particular amino acid.

Thus the invention relates to:
1. A replicating extrachromosomal element which contains the ilvE gene isolated from E. coli ATCC 11303.
2. The use of the extrachromosomal element specified under 1) for the synthesis of aliphatic aminotransferase.
3. The use of the extrachromosomal element specified under 1) for the overproduction of branched-chain amino acids in microorganisms, which comprises
   a) introduction of the extrachromosomal element into a microorganism,
   b) expression of the ilvE gene in this microorganism, and synthesis of an active aliphatic transaminase, and
   c) bringing about the amination of the appropriate keto precursors by the transaminase.

The invention is explained in detail in the description which follows and defined in the patent claims.

It is possible to use not only the wild type E. coli ATCC 11303 but also its variants and mutants. For example, it is also possible to use a strain which has been mutated by known methods [E. Adelberg et al., Biochem. Biophys. Res. Comm. 18, 788 (1965)] and has been selected for over-production of branched-chain amino acids. The aliphatic aminotransferase from E. coli ATCC 11303, for which the ilvE gene codes, synthesizes valine, leucine and isoleucine, inter alia, from the relevant keto precursors by transferring an amino group from glutamate. Moreover, it is also possible to synthesize phenylalanine and glutamic acid using the aliphatic transaminase. Apart from the product of the ilvE gene, further transaminases are found in E. coli cells as products of other genes.

For example, the aromatic transaminase, the product of the tyrB gene, catalyzes the synthesis of phenylalanine, tyrosine, aspartate and leucine, and the product of the aspC gene catalyzes the synthesis of aspartate, glutamate, phenylalanine and tyrosine. However, each of the said transaminases also exhibits a weak activity in the synthesis of amino acids which in fact ought more specifically to be assigned to one of the two other transaminases.

In order further to increase the synthesis of branched-chain amino acids, the ilvE gene, which codes for the aliphatic aminotransferase, is cloned. This is achieved by isolating the DNA from E. coli ATCC 11303. Partial digestion of the DNA is followed by the resulting fragments, which have sizes which vary in the range 20–30 kb, being ligated into a cosmid with a replicon which confers a wide host range, and packaging into the heads of phage λ. The cosmid pIMS 6026 is preferably used. The cosmid pIMS 6026 is derived from the cosmid pLAFR 1 (ATCC 37167) by the commercially available EcoRI fragment (Pharmacia, Uppsala, Sweden) on which is located the kanamycin-resistance gene of the transposon Tn 903 having been cloned into the single EcoRI cleavage site of the cosmid pLAFR 1. It is possible by digestion with BamHI and subsequent religation to delete most of the EcoRI fragment so that a short piece of DNA remains as an insertion in which a BamHI cleavage site is flanked by 2 EcoRI cleavage sites. This BamHI cleavage site, which is not present on the cosmid pLFAR 1, can be used for clonings. The cosmids are introduced into the microorganism by incubation of the packaged cosmids with an appropriately prepared E. coli DG 30 suspension. E. coli DG 30 has a deficiency of the three transaminases aspC, ilvE and tyrB. Hence, although the strain grows without difficulty on complete medium, for growth on minimal medium various amino acids must be supplied from outside because it cannot synthesize them itself. With appropriate choice of the medium it is possible with the aid of the strain to examine whether a DNA which has been taken up from outside is able to complement the chromosomal defect for a particular transaminase. The introduction of the ilvE gene is detected by growth of the E. coli DG 30 on a tyrosine-free minimal medium. Only clones which are able to complement their chromosomal defect for the synthesis of tyrosine by uptake of DNA which contains aspC, tyrB or ilvE and originates from the strain E. coli ATCC 11303 are able to grow on this medium. The three transaminases which are coded for by the genes aspC, tyrB and ilvE differ in their substrate specificity, although all three of them are able to form tyrosine.

The aromatic transaminase, which is coded for by the gene tyrB, is unable, for example, to form isoleucine from the keto precursor but is able to synthesize leucine in good yields from the corresponding keto precursor. The transaminase which is coded for by the gene aspC is unable to form isoleucine nor is it efficient in the conversion to leucine. However, the ilvE gene product produces a good yield of isoleucine.

Accordingly, it is possible to distinguish between the individual clones in respect of the contained transaminase by growth on a minimal medium which is supplemented by the amino acids essential for metabolism apart from one amino acid which is characteristic of the particular gene. Clones of the DG 30 strain which contain the ilvE gene are selected out in this way.

It is now necessary to check whether the clones really do possess the ilvE gene. It is necessary for this to isolate the plasmid DNA from the clones. However, isolation from the strain DG 30 is possible only with difficulties. Although it is possible to obtain plasmid DNA, the yields are only low. Thus, after minilysis, an E. coli strain is transformed with the cosmid DNAs from the clones of interest, and it is then possible to reisolate the introduced DNA in good yields from this strain. E. coli DH1 (ATCC 33849) is particularly suitable for this purpose.

In the next step, the reisolated cosmid DNA is ligated with a vector of high copy number. It is known from the chromosomal gene map of the strain E. coli K12 that the ilvE gene is located on a SalI-SmaI framgnet. This fragment contains only the structural gene of ilvE but does not contain the natural promoter. It is possible that this is also the case in E. coli ATCC 11303. For this reason, the vector wwhich is preferably used is a multicopy plasmid which allows cloning of the SalI-SmaI fragment in such a way that the cloned sequence comes under the control of a promoter present on the plasmid. pBR322, whose sequence is known and which is commercially available, is particularly preferred.

The cosmid DNA is completely digested with the enzymes SalI and SmaI, and the vector is completely digested with the restriction enzymes SalI and PvuII. The two DNAs are mixed and ligated together, and the product is used to transform competent cells of a host organism in which it is intended to raise the production of branched-chain amino acids. Enterobacteria are preferably used, in particular E. coli, and E. coli ATCC 11303 and its mutants and variants are particularly preferred. Resistant colonies are selected using ampicillin, plasmid DNA is isolated from the appropriate colonies by minilysis, and the vector DNA is examined for a change in size by complete digestion with the restriction enzyme SalI. Restriction analysis is carried out to ensure that all the SalI-SmaI fragments contained in the original DNA section have been subcloned in this way. Clones which each contain one of these SalI-SmaI fragments are then tested, using a test known from the literature (Duggan et al., Anal. Biochem. 51 (1973) 67-79) for the activity of the aliphatic transaminase, that is to say the gene product of ilve. It is possible in this way to achieve an increase in the ilvE activity by a factor of more than 10. It can be shown, by agarose gel electrophoresis, that the vector of the host strain contains an ATCC 11303 fragment about 1 MD in size.

The invention is described in detail in the examples which follow. Unless otherwise specified, percentage data relate to weight.

EXAMPLE 1

Isolation and digestion of the cosmid pIMS 6026 from E. coli

The procedure used for the isolation of the cosmid pIMS 6026 from E. coli was either that of Humphreys et al. [Biochim. Biophys. Acta 383, 457-63 (1975)] or an alkaline lysis by the method of Birnboim and Doly [Nucleic Acids Res. 7: 1513 (1979)] on a 10 times larger scale. In each case, the plasmid DNA was purified at least once by CsCl/EtBr density gradient centrifugation.

The cosmid pIMS 6026 was completely digested with the restriction enzyme BamHI using the procedure given by the manufacturer, New England Biolabs. To check the completeness of this digestion, an aliquot of the restriction mixture was applied to a 0.8% agarose gel and subjected to electrophoresis. The appearance of only one band after staining with ethidium bromide and irradiation with short-wavelength UV light (254 nm) served to indicate complete digestion. The restriction enzyme was removed from the digested cosmid DNA by treatment with phenol, and the DNA was precipitated with ethanol, washed with 70% strength ethanol, dried in vacuo and then taken up in a suitable volume of TE buffer (10 mM tris; 1 M EDTA, pH 8.0). A treatment with alkaline phosphatase was then optionally carried out by the method given by the manufacturer, Boehringer Mannheim. After addition of 1 µl of alkaline phosphatase (CIP), the reaction mixture was incubated at 37° C. for 30 minutes and the enzyme was removed by phenol treatment, and the DNA was purified as described above. It was finally resuspended in TE buffer.

EXAMPLE 2

Partial digestion of the DNA from E. coli ATCC 11303

The total DNA from E. coli ATCC 11303 was isolated by the method of Marmur in J. Mol. Biol. 53, 155-162 (1961).

The isolated total DNA was partially digested with the restriction enzyme Sau3A so that the resultant fragments were mainly in the size range 20-30 kb. Preliminary tests were carried out to establish the optimal ratio of DNA and enzyme for this purpose and the optimal duration of action of the enzyme on the DNA. The appropriate procedure is described in the publication "focus" on page 3 of Vol. 7, No. 2 (1985), which is published by BRL. After the reaction time which had been found to be optimal had elapsed, the enzyme was decomposed by heating at 65° C. for a 10-minute period, and the formation of DNA fragments in the desired size range was checked by agarose gel electrophoresis using suitable DNA markers, for example with phage λ DNA digested with EcoRI.

EXAMPLE 3

Ligation of the restriction mixtures

The total DNA from E. coli ATCC 11303, which had been partially digested with Sau3A, was mixed in a molar ratio of about 1:5 with pIMS 6026 cosmid DNA which had been completely cleaved with BamHI and treated with alkaline phosphatase. The resulting mixture was mixed with a several-fold concentrated buffer as stated by New England Biolabs in such a way that an ionic concentration optimal for the enzyme T4 DNA ligase resulted, and the mixture was incubated with 1 µl of the enzyme at 16° C. for at least 14 hours. The total volume of this mixture was 50 µl with a total DNA concentration of 20 µg/ml.

EXAMPLE 4

Phage λ packaging

The ligase reaction was followed by in vitro packaging of DNA obtained as in Example 3 into phage λ heads. The extracts from two different bacterial strains which are necessary for this purpose can be obtained by the method of Hohn, B., in Wu, R., editor: Recombinant DNA, Methods in Enzymology, Vol. 68, Academic Press, New York, pages 299-309 (1979) or purchased from Boehringer Mannheim or Amersham Buchler, Braunschweig.

3 µl of the mixture obtained as in Example 3 were thoroughly mixed, while cooling in ice, with bacterial extracts supplied by Amersham, which had been thawed immediately beforehand. The mixture was incubated at 20° C. for 30-60 minutes, and then 200 µl of SM buffer (100 mM NaCl, 10 mM MgSO4, 50 mM tris-HCl (pH 7.5), 0.01% gelatin) were added. This mixture was either used directly in a transduction reaction or stored at 4° C., after addition of 10 µl of chloroform, until used later.

EXAMPLE 5

Transduction of *E. coli* DG 30

0.4% maltose was added to 5 ml of L broth, composed of 1% Bacto Tryptone, 0.5% yeast extract and 0.5% NaCl, and the mixture was inoculated with 50 µl of a liquid culture of *E. coli* DG 30 in the stationary phase of growth. It was incubated at 37° C. for 12 hours, until the early stationary phase was reached. The bacteria were spun down and carefully resuspended in 2.5 ml of an aqueous solution which was 10 millimolar in MgCl2. 10 µl of the mixture from Example 4 were mixed with 20 µl of the concentrated bacterial suspension, and the mixture was incubated at room temperature for 50 minutes.

Then 200 µl of L broth were added, and the mixture was incubated at 37° C. for 1 hour, shaking occasionally. 50 µl aliquots of the mixture were plated out on L broth agar which contained 20 µg/ml tetracycline. The plates were incubated at 37° C. for at least 12 hours. With the procedure described, it was possible to obtain a mean of 1,000 colonies from a mixture.

EXAMPLE 6

Selection of *E. coli* DG 30 with an aspC or ilvE or tyrB gene

About 800 colonies, which had been obtained after transduction of *E. coli* DG 30 by the process described on L broth agar which contained 20 µg/ml tetracycline, were "picked" onto minimal agar. The minimal agar was composed of M9 medium with glucose (Miller, Experiments in Molecular Genetics, Cold Spring Harbor, 1972) which had been supplemented with the amino acids isoleucine, leucine, valine, aspartic acid and phenylalanine. However, the amino acid tyrosine, which the strain DG 30 is likewise now unable to synthesize, was not added to the medium. Of the 800 "picked" colonies, 7 were able to grow on the minimal medium.

To distinguish the three possible genes aspC, ilvE and tyrB in *E. coli* DG 30, these 7 colonies were again "picked" onto the abovementioned minimal medium which had been supplemented with the listed amino acids apart from one in each case, for which one of the transaminases which is coded for by one of the genes shows substrate specificity. The result is shown in the table which follows:

| Clone | Minimal medium with supplements apart from | | | | Presumed gene |
| --- | --- | --- | --- | --- | --- |
| | Asp | Leu | Ile | Tyr | |
| 1 | + | + | − | + | tyrB |
| 2 | + | + | − | + | tyrB |
| 3 | − | +− | + | +− | ilvE |
| 4 | − | +− | + | +− | ilvE |
| 5 | + | + | − | + | tyrB |
| 6 | + | + | − | + | tyrB |
| 7 | − | +− | + | +− | ilvE |

+ = satisfactory growth
+− = poor growth
− = no growth

EXAMPLE 7

Localization of the ilvE gene

Cosmid DNA was obtained, by minilysis by the method of Maniatis et al., Cold Spring Harbor, pages 366-370 (1982), from clones 1 to 7 which had been obtained as in Example 6. This cosmid DNA was then introduced into *E. coli* DH1 (ATCC 33849), from which it could be reisolated again in good yields.

Plasmid DNA, which had originally been obtained from clone 3 of *E. coli* DG 30 (see Example 6), was isolated from the strain *E. coli* DH 1 transformed with this DNA, and was completely digested with the restriction enzymes SalI and SmaI, following the instructions of the manufacturer, New England Biolabs. The vector pBR322 was likewise completely digested with the enzymes SalI, PvuII and AvaI. The digestion with AvaI is intended to prevent back-ligation of the SalI-SmaI fragment originating from pBR322 into the vector. The two DNAs were mixed and ligated together in the manner already described in Example 4, and competent cells of the strain *E. coli* ATCC 11303 were transformed with an aliquot of the ligase mixture, for example 10 µl. Resistant colonies were selected on L broth plates which contained 50 µg/ml ampicillin, plasmid DNA was isolated by minilysis, and the vector DNA was checked for a change in size by complete digestion with the restriction enzyme SalI.

EXAMPLE 8

Examination of the transaminase activity

The clones obtained as in Example 7 were tested, using the specified test, for the activity of aliphatic transaminase, that is to say the gene product of ilvE. The untransformed starting strain *E. coli* ATCC 11303 was used for comparison. This measurement showed a marked increase in ilvE activity in one case, specifically by a factor of greater than 10, compared with the starting strain *E. coli* ATCC 11303.

It was possible to show, by agarose gel electrophoresis using suitable markers, that the strain which exhibited increased ilvE gene activity contained a pBR322 vector which contained an incorporated fragment about 1 MD in size from ATCC 11303. When the isolated plasmid DNA was again used to transform the plasmid-free strain *E. coli* ATCC 11303, it was possible in every case to observe an increase in the ilvE gene activity by a factor of greater than 10.

EXAMPLE 9

Temperature-inducible expression of the ilvE gene

The DNA fragment from *E. coli* ATCC 11303 which is cloned as the SalI-SmaI fragment of about 1 MD carries the ilvE gene without the natural promoter. Rather, the expression of the gene is effected after cloning in pBR322 which has been digested with SalI and PvuII by transcription starting from the tetracycline promoter from pBR322, followed by translation of the mRNA corresponding to ilvE. Although the tetracycline promoter from pBR322 is relatively strong and gives good protein yields, it cannot be regulated by changing the temperature. In order to make it possible to use temperature to regulate the expression of ilvE, the SalI-EcoRI fragment carrying the tetracycline promoter at the 5' end of the ilvE gene is replaced by a SalI-EcoRI fragment on which are located the $P_R$ promoter of phage λ and the temperature-sensitive repressor gene $cI_{857}$. The vector pCQV2 acts as source of this fragment (Queen, J. Molec. and Applied Genetics 2 (1983) 1–10). The vector pCQV2 is completely digested with the restriction enzymes EcoRI and SalI. The vector obtained as in Example 8 is likewise completely digested with these enzymes. This entails the particular enzymes being added simultaneously to the DNA, and the mixture being incubated in REB buffer [50 mM NaCl, 10 mM tris-HCl, pH 7.5; 6 mM 2-mercaptoethanol, 6 mM $MgCl_2$, 100 μg/ml bovine serum albumin, 0.01% non-ionic surfactant (®Triton X-100)] at 37° C. for one hour. The total volume of the mixtures in 50 μl, with a DNA concentration of 20 μg/ml. The completeness of the digestions is checked by agarose gel electrophoresis of a 5 μl aliquot of each of the mixtures. The two mixtures are heated at 65° C. for 10 minutes, the restriction enzymes are removed by phenol treatment, and the cut plasmid DNA is purified by ethanol precipitation and subsequent washing with 70% strength ethanol. After drying in vacuo, the respective DNAs are resuspended in 50 μl of TE buffer, and 10 μl of each mixture are pipetted into the same vessel. The mixture is adjusted to the medium recommended by the manufacturer (New England Biolabs) as optimal for the enzyme T4 DNA ligase, and 10 units of the enzyme T4 DNA ligase are added. The mixture is incubated at 16° C. for 16 hours, and then competent cells of the *E. coli* strain HB 101 are transformed with a 10 μl aliquot of the ligase mixture. Ampicillin-resistant colonies are selected and, after minilysis, plasmid DNA from these clones is subjected to a double digestion with the restriction enzymes SalI and EcoRI. It is possible by agarose gel electrophoresis to identify clones which contain plasmids with the expected fragment pattern.

Two of the clones identified in this way are cultured in LB medium (Miller, loc. cit.) at an incubation temperature of 30° C. or 37° C. The figure for the enzyme activity of the ilvE gene product from bacteria cultured at 37° C. which emerges on investigation is a factor of 5–10 above that of a plasmid-free comparison strain. The figures measured on investigation of the enzyme activity of the clone cultured at 30° C. are virtually identical to those of a plasmid-free comparison strain. In contrast, if the bacteria are cultured at 30° C., and then the temperature of the culture is increased to 45° C. by shaking in a waterbath at 65° C., and the culture is then further incubated at 37° C. for 2 hours, the enzyme activities which can be measured are increased at least 10-fold.

We claim:

1. A replicating extrachromosomal element containing the ilvE gene, isolated from *E. coli* ATCC 11303, and a multicopy plasmid.

2. *E. coli* ATCC 11303, and its variants and mutants, transformed with the extrachromosomal element as claimed in claim 1.

* * * * *